United States Patent [19]

Lindegren

[11] Patent Number: 5,609,623
[45] Date of Patent: Mar. 11, 1997

[54] ELECTRODE DEVICE FOR INTRACARDIAC STIMULATION OF HEART TISSUE AND/OR SENSING HEART SIGNALS HAVING CONDUCTIVE SURFACES RELATIVELY POSITIONABLE WITH RESPECT TO EACH OTHER BY A CONTROL ELEMENT

[75] Inventor: Ulf Lindegren, Enskededalen, Sweden

[73] Assignee: Pacesetter AB, Solna, Sweden

[21] Appl. No.: 517,182

[22] Filed: Aug. 21, 1995

[30] Foreign Application Priority Data

Aug. 19, 1994 [SE] Sweden .................. 9402775

[51] Int. Cl.⁶ .................................................. A61N 1/36
[52] U.S. Cl. ............................................. 607/128; 607/126
[58] Field of Search ........................ 607/115, 116, 607/119, 122, 123, 125, 126, 128, 41, 47; 128/642

[56] References Cited

U.S. PATENT DOCUMENTS

| 3,754,555 | 8/1973 | Schmitt ................... 607/128 |
| 3,976,082 | 8/1976 | Schmitt ................... 607/128 |
| 4,254,764 | 3/1981 | Neward ................... 128/642 |
| 4,289,138 | 9/1981 | Halvorsen . | |
| 4,501,276 | 2/1985 | Lombardi ................ 128/642 |
| 4,567,901 | 2/1986 | Harris . | |
| 4,848,352 | 7/1989 | Pohndorf et al. . | |
| 4,862,887 | 9/1989 | Weber et al. ........... 128/642 X |
| 4,940,064 | 7/1990 | Desai ....................... 607/122 |
| 5,237,996 | 8/1993 | Waldmann et al. ..... 128/642 |
| 5,306,292 | 4/1994 | Lindegren . | |
| 5,327,889 | 7/1994 | Imran ..................... 607/122 X |

Primary Examiner—Jeffrey R. Jastrzab
Attorney, Agent, or Firm—Hill, Steadman & Simpson

[57] ABSTRACT

An electrode device, for intracardiac stimulation of heart tissue and/or sensing heart signals in a patient, has an electrode cable containing at least two elongate, flexible conductors, insulated from each other, and with an electrode head, arranged at the distal end of the electrode cable and at least two conductive surfaces, each connected to a separate conductor. In order to permit the distance between the conductive surfaces to be varied over a continuous range, simply and easily, the electrode head has at least two parts, moveable in relation to each other, each part being provided with at least one conductive surface, and the a control element is movably arranged at the distal end of the electrode cable immediately behind the electrode head, so any change in the position of the control element causes the control element to act on the parts of the electrode head such that the distance between the conductive surfaces is varied.

11 Claims, 2 Drawing Sheets

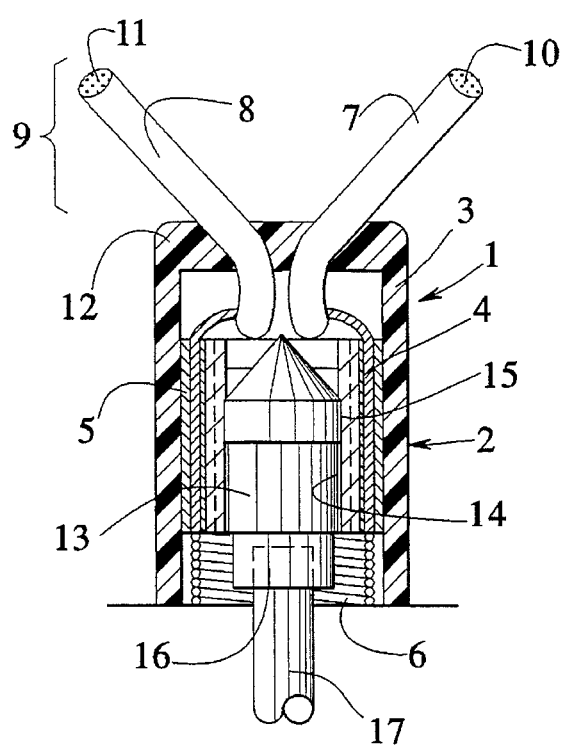
FIG. 1
FIG. 3
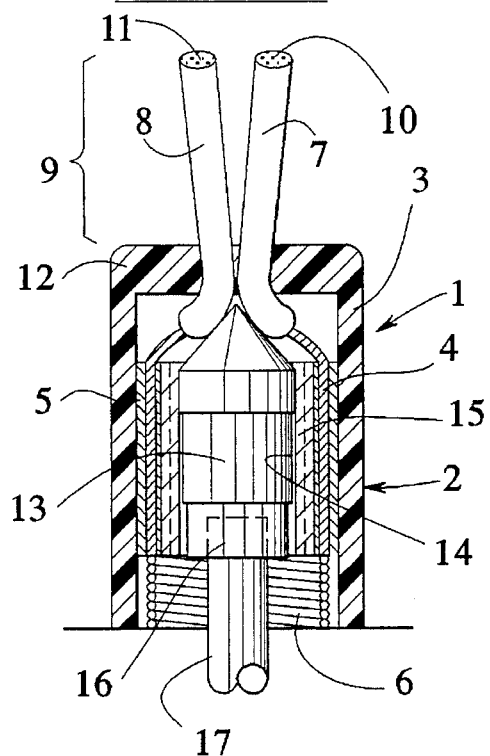
FIG. 2
FIG. 4

5,609,623

ELECTRODE DEVICE FOR INTRACARDIAC STIMULATION OF HEART TISSUE AND/OR SENSING HEART SIGNALS HAVING CONDUCTIVE SURFACES RELATIVELY POSITIONABLE WITH RESPECT TO EACH OTHER BY A CONTROL ELEMENT

BACKGROUND OF THE INVENTION

1. Field of the Invention

The present invention relates to an electrode device for intracardiac stimulation of heart tissue and/or sensing heart signals in a patient, of the type having an electrode cable containing at least two elongate, flexible conductors, insulated from each other, and with an electrode head, arranged at the distal end of the electrode cable and provided with at least two conductive surfaces, each connected to a separate conductor.

2. Description of the Prior Art

An electrode device of the above general type is disclosed in U.S. Pat. No. 5,306,292. In one embodiment, the electrode head of this known electrode device is equipped with a number of punctiform conductive surfaces. In a second embodiment, the electrode head is formed by two conductive bodies, one of the bodies being a centrally arranged projecting part which is insulated from the other conductive body. In another embodiment disclosed in this patent, one of the conductive surfaces is arranged on the end of the electrode cable, and the second conductive surface is formed by part of a traumatic, helical fixing means on the electrode head.

U.S. Pat. No. 4,848,352 describes another pacemaker electrode of the type initially described, with a head subdivided into sections of conductive material insulated from each other.

The conductive surfaces in these known electrode devices serve as stimulation surfaces and as sensing surfaces. In some of the embodiments of these known electrode devices, the distance between the stimulation surfaces and, accordingly, even the distances between a stimulation surface and a sensing surface, can be varied when different conductive surfaces are connected by a pacemaker having a switching stage. The distance between stimulation surfaces is governed to a large degree by the system's impedance, i.e. the larger the distance between stimulation surfaces, the larger the impedance obtained. This means that the physician might wish to reduce the distance between stimulation surfaces, if e.g. the threshold value is too high, so current increases and voltage decreases. In the prior art electrode devices cited herein, the change in distance between stimulation surfaces on the head of the electrode device is very limited, since the electrode cable can only hold a limited number of conductors, thereby limiting the number of conductive surfaces on the electrode head. Moreover, the change in distance is predetermined, since the conductive surfaces are permanently arranged on the electrode head with a fixed distance between them.

SUMMARY OF THE INVENTION

An object of the invention is to achieve an electrode device of the type initially described in which the distance between the conductive surfaces can be varied continuously, simply and as needed.

This object is achieved in accordance with the principals of the present invention in an electrode device having an electrode head formed by at least two parts, moveable in relation to each other, each part being provided with at least one conductive surface, and the electrode device having control element movably arranged at the distal end of the electrode cable immediately behind the electrode head. Any change in the position of the control element causes the control element to act on the parts of the electrode head in such a way that the distance between the conductive surfaces is varied. With this structure, the physician can, after the electrode device has been implanted, use the control means to change the distance between the conductive surfaces with infinite variation (i.e., with no discontinuities) and, using a measurement instrument, to set the distance between the conductive surface with high accuracy to achieve an optimum threshold value for the patient.

According to a preferred embodiment of the invention, each moveable part on the electrode head is formed of pin-shaped parts, made of an electrically conductive material, constituting the conductive surface at least in part. This results in an electrode head with a very simple structure.

In another embodiment of the invention which is particularly simple in structure, the end of the electrode cable is provided with an elastic, plastic material in which the electrode head's moving parts are resiliently mounted opposite each other.

In another embodiment of the invention, the distal end of the control means is conical. When the control means are then advanced, the rear ends of the moveable parts are forced apart, thereby changing the distance between the conductive surfaces. This makes it possible to achieve very accurate setting of the distance between the conductive surfaces in a smooth and simple manner.

This setting accuracy is also achieved when the control means are formed by an eccentric cam arranged between the rear ends of the parts. When the eccentric cam is turned, the distance between the rear ends, and accordingly the distance between the conductive surfaces, changes, so continuous changes in distance can be achieved.

In an other embodiment of the invention, each moveable part is disposed in a separate channel arranged at the distal end of the electrode cable, the channels being arrayed such that longitudinal displacement of the parts changes the distance between the conductive surfaces. In this embodiment, these parts can even be completely retracted into the electrode cable so the parts are enclosed by the electrode cable during the cable introduction phase.

DESCRIPTION OF THE DRAWINGS

FIGS. 1 and 2 show the distal end of a first embodiment of an electrode device according to the invention in longitudinal section and with the moveable parts respectively in a retracted position and in a deployed position.

FIGS. 3 and 4 show the distal end of a second embodiment of an electrode device according to the invention in longitudinal section and with the moveable parts respectively in a retracted position and in a deployed position.

DESCRIPTION OF THE PREFERRED EMBODIMENTS

Figure 5:
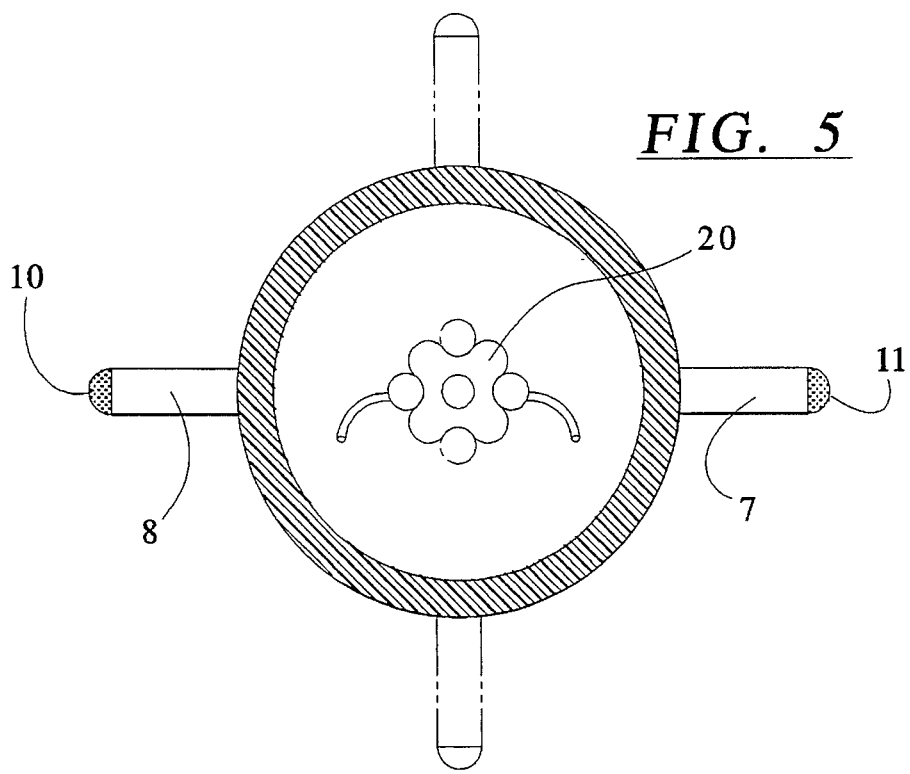
FIG. 5 shows a cross-section along the line V—V in FIG. 4.

FIG. 1 shows the distal end 1 of an electrode device for intracardiac stimulation of heart tissue and/or sensing heart signals in a patient. The electrode device includes an electrode cable 2 with insulation 3 in which two elongate, flexible conductors 4 and 5, insulated from each other, are contained. The conductors 4 and 5 preferably are helically wound parallel to each other and form the inner wall of a channel 6 extending the entire length of the electrode cable 2. The conductors 4 and 5 are respectively connected to pin-shaped parts 7 and 8 each having a curved section and each made of an electrically conductive material. These pin-shaped parts 7 and 8 form an electrode head 9. The pin-shaped parts 7 and 8 are for the most part covered by an insulated surface coating, except for their respective exposed distal ends, which form conductive surfaces 10 and 11 for stimulating heart tissue and/or sensing heart signals in a patient. An elastic, plastic material, e.g. silicone, in which the pin-shaped parts 7 and 8 are resiliently mounted opposite each other, is provided at the distal end 12 of the electrode cable 2. In FIG. 1, the pin-shaped parts 7 and 8 are shown in a position in which they are not being displaced on by any means and in which the conductive surfaces 10 and 11 are at a maximum distance from each other.

The electrode device is also equipped with a control element 13 which moves the pin-shaped parts 7 and 8 and causes the distance between the conductive surfaces 10 and 11 to change. The control element 13, which is arranged in the channel 6 immediately behind the proximal ends of the pin-shaped parts 7 and 8, is cylindrical and is provided with a thread 14 which matches a thread 15 arranged along a section of the channel 6. The distal end of the control element 13 is conical, and its proximal end is provided with a hexagonal socket 16 into which the distal end of a stylet 17 fits.

When a change in the distance between the conductive surfaces 10 and 11 is desired, the stylet 17 is inserted into the hexagonal socket 16. By rotating the stylet, the physician can then advance the control element 13, thereby pushing the conical end between the proximal ends of the pin-shaped parts 7 and 8 and forcing the ends thereof apart. The change in distance between the conductive surfaces 10 and 11 then depends on the distance the control element 13 is pushed between the ends of the pin-shaped parts 7 and 8.

FIG. 2 shows the control element 13 maximally advanced between the ends of the pin-shaped parts 7 and 8, so the distance between the conductive surfaces 10 and 11 is minimized in this embodiment. The maximum and minimum distances between the conductive surfaces 10 and 11 are governed by the length and curvature of the pin-shaped parts 7 and 8. FIG. 2 shows a position which the pin-shaped parts 7 and 8 can advantageously assume during the implantation of the electrode device, since the pin-shaped parts 7 and 8 in this position do not laterally protrude outside the electrode cable 2.

If the position shown for the pin-shaped parts 7 and 8 in FIG. I creates an optimum distance between the conductive surfaces 10 and 11 for stimulating heart tissue, the pin-shaped parts 7 and 8 in this position can serve as fixing means for the electrode cable 2. This embodiment only shows and describes two pin-shaped parts 7 and 8, each with one conductive surface 10 and 11. The electrode head 9 could, however, have a large number of such pin-shaped parts, each with a conductive surface, and each being resiliently mounted in the distal end 12 of the cable 2 so as to be adjustable with the common control element 13.

FIGS. 3 and 4 show the distal end of an electrode device 18 which only differs from the electrode device 1 in FIGS. I and 2 by having a different control element. The illustrated components of the electrode device 18, except for the control element, thus have the same reference designations as in FIGS. I and 2. The control element of the electrode device 18, has an eccentric cam 20 which is rotatingly arranged in the channel 6 between the rear ends of the pin-shaped parts 7 and 8. The eccentric cam 20 is connected by a shaft 21 to a rotation coupling 22 with a hexagonal socket 23 into which the stylet 17 can be inserted. The eccentric cam 20 and the rotation coupling 22 with the shaft 21 are rotatingly arranged in a holder 24 attached to the surrounding channel wall. When the physician wishes to change the distance between the conductive surfaces 10 and 11, he or she inserts the stylet into the hexagonal socket 23 of the rotation means 22 and rotates the stylet 17 in either direction. The peripheral surface of the eccentric cam 20 then displaces the rear ends of the pin-shaped parts 7 and 8, thereby changing the distance between the distal ends having the conductive surfaces 10 and 11. In FIG. 3, the eccentric cam 20 has been turned to a position in which the rear ends of the pin-shaped parts 7 and 8 touch the part of the peripheral surface at the largest distance from the shaft 21. In this position, the conductive surfaces 10 and 11 are separated by a minimum distance. The electrode cable 2 can advantageously be implanted with the pin-shaped parts in this position.

FIG. 4 shows a pin-shaped parts position in which the conductive surfaces 10 and 11 are arranged at a maximum distance from each other. The rear ends of the pin-shaped parts 7 and 8 now touch the part of the peripheral surface of the eccentric cam 20 closest to the shaft 21, in this pin-shaped parts position, the pin-shaped parts 7 and 8 can even serve as fixing means.

FIG. 5 is a section taken along the line V—V in FIG. 4. This view shows the shape of the eccentric cam 20. FIG. 4 also shows that the eccentric cam 20 can control more pin-shaped parts than just the pin-shaped parts 7 and 8 described. Two additional pin-shaped parts are indicated with dotted lines. The shape of the eccentric cam 20 is not restricted to the one shown but can differ, depending on the number of pin-shaped parts and the way the pin-shaped parts are to be displaced in relation to each other.

Figure 6:
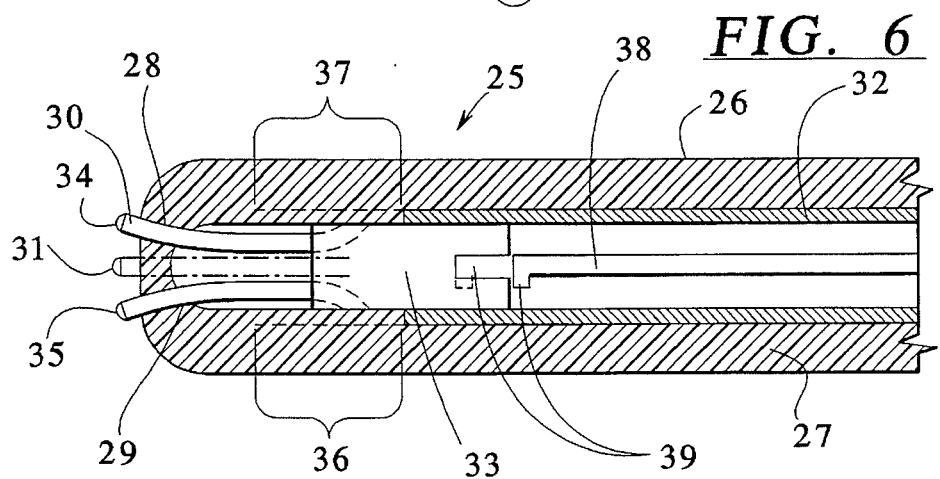
FIGS. 6 and 7 show the distal end of a third embodiment of an electrode device according to the invention, in longitudinal section and with the moveable parts respectively in a retracted position and in a deployed position.
Figure 7:
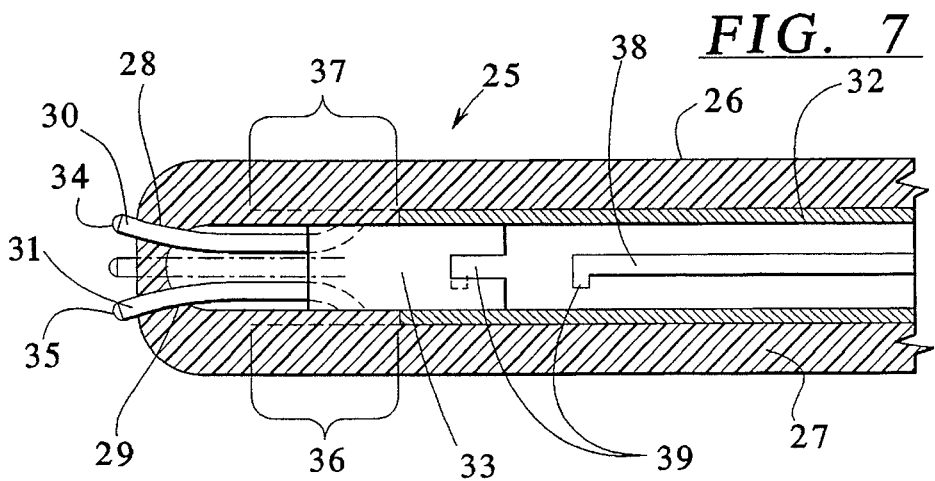

FIGS. 6 and 7 show another embodiment of an electrode device 25 which differs from the electrode devices I and 18 illustrated and described above. This electrode device 25 has an electrode cable 26 with a sleeve of insulation 27 which also seals the distal end of the electrode cable 26, except for a number of channel-like holes 28 and 29. This electrode device 25 also has a channel 32 which extends the entire length of the electrode cable 26. A cylindrical control element 33 is slidingly arranged in the channel 32 immediately behind the end of the electrode cable 26. Pin-shaped parts 30 and 31 with respective conductive surfaces 34 and 35 are arranged at the distal end of the control element 33. Each of the pin-shaped parts 30 and 31 runs in a separate channel 28 and 29, the channels 28 and 29 being arrayed such that longitudinal movement of the control element 33 and the pin-shaped parts 30 and 31 changes the distance between the conductive surfaces 34 and 35. The pin-shaped parts 30 and 31 can even be given an inherent curve so a relatively long distance is achieved between the conductive surfaces 34 and 35 when the protrusion of the pin-shaped parts out of the channels 28 and 29 is at a maximum. Each of the pin-shaped parts 30 and 31 is preferably connected through the cylindrical control element 33 to a separate conductor forming the inner wall of the channel 32 and whose ends are exposed as contact rails along respective distances 36 and 37, the respective proximal ends of the pin-shaped parts 30 and 31 being in constant contact with these contact rails. The control element 33 is moved with a stylet 38. The stylet 38 and the control element 33 are interconnected with, e.g., a bayonet lock 39. The external diameter of the control element 33 is such, in relation to the diameter of the channel 32, that the control element 33 can only be moved with the stylet 38. In FIG. 6 the pin-shaped parts 30 and 31 have been moved so the distance between conductive surfaces 34 and 35 is at a minimum. The pin-shaped parts 30 and 31 can also be fully retracted into the respective channels 28 and 29, thereby facilitating implantation of the electrode device. In FIG. 7, the pin-shaped parts 30 and 31 have been advanced, thereby changing the distance between the conductive surfaces 34 and 35. If the control element 33 is advanced even further, a longer distance is achieved between the conductive surfaces 34 and 35. This electrode device 25 can also be equipped with a large number of pin-shaped parts with attendant conductive surfaces, as designated by the dashdotted outline of further pin-shaped parts.

Other embodiments of the electrode device are conceivable within the scope of the invention. The main feature is that the distance between the described conductive surfaces is continuously variable, making it possible to achieve an optimum threshold value for the patient. The electrode device according to the invention is preferably connected to a pacemaker of the type having a switching stage with which the different conductive surfaces can be connected (activated) as desired so the distance can be varied between the stimulation surfaces, and accordingly the distance between a stimulation surface and a sensing surface can also be varied.

Although modifications and changes may be suggested by those skilled in the art, it is the intention of the inventor to embody within the patent warranted hereon all changes and modifications as reasonably and properly come within the scope of his contribution to the art.

I claim as my invention:

1. An electrode device for in vivo electrical interaction with cardiac tissue, comprising:

an electrode cable containing at least two elongate, flexible conductors insulated from each other, said electrode cable terminating in an electrode head;

said electrode head including at least two moveable, rigid parts mounted in said electrode head so as to be moveable relative to each other, each rigid part carrying at least one electrically conductive surface thereon adapted for in vivo interaction with cardiac tissue, the conductive surfaces being respectively electrically connected to said conductors in said electrode cable; and control means disposed in said electrode cable immediately behind said electrode head for mechanically acting on said rigid parts for causing a distance between the respective conductive surfaces carried by said rigid parts to be continuously varied as a position of said control means in said electrode cable is changed; and means for manually changing the position of said control means in said electrode cable.

2. An electrode device as claimed in claim 1 wherein each of said moveable rigid parts of said electrode head consists of an electrically conductive pin-shaped part, each pin-shaped part having an exterior surface comprising said electrically conductive surface.

3. An electrode device as claimed in claim 1 wherein said electrode head comprises an element consisting of elastic, plastic material in which said moveable rigid parts are resiliently mounted spaced from each other.

4. An electrode device as claimed in claim 1 wherein at least one of said moveable rigid parts has a curved section.

5. An electrode device as claimed in claim 1 wherein said electrode cable has a longitudinal axis extending along a length thereof, wherein each of said moveable rigid parts has a rear end extending immediately behind said electrode head, and wherein said control means comprises a conical element abutting said rear ends of said moveable rigid parts, and wherein said means for changing the position of said control means comprises means for advancing said conical element along said longitudinal axis towards said electrode head for mechanically interacting with said rear ends of said moveable rigid parts to change the distance between the conductive surfaces.

6. An electrode device as claimed in claim 1 wherein said electrode cable has a longitudinal axis extending along a length thereof, wherein each of said moveable rigid parts has a rear end extending immediately behind said electrode head, and wherein said control means comprises an eccentric cam disposed for engaging said rear ends of said moveable rigid parts, and wherein said means for changing the position of said control means comprises means for rotating said eccentric cam around said longitudinal axis for changing the distance between said conductive surfaces.

7. An electrode device as claimed in claim 1 wherein said electrode cable comprises a plurality of separate channels, each channel receiving one of said moveable rigid parts, wherein said control means comprises an element for forcing said moveable rigid parts through the respective channels, and wherein said means for changing the position of said control means comprises means for pushing said control element toward said electrode head.

8. An electrode device for in vivo electrical interaction with cardiac tissue, comprising:

an electrode cable containing at least two elongate, flexible conductors insulated from each other, said electrode cable terminating in an electrode head;

said electrode head including an element consisting of elastic, plastic material and at least two moveable parts resiliently mounted in said element spaced from each so as to be moveable relative to each other, each part carrying at least one electrically conductive surface thereon adapted for in vivo interaction with cardiac tissue, the conductive surfaces being respectively electrically connected to said conductors in said electrode cable; and control means disposed in said electrode cable immediately behind said electrode head for mechanically acting on said parts for causing a distance between the respective conductive surfaces carried by said parts to be continuously varied as a position of said control means in said electrode cable is changed; and means for manually changing the position of said control means in said electrode cable.

9. An electrode device as claimed in claim 8 wherein each of said moveable parts of said electrode head consists of an electrically conductive pin-shaped part, each pin-shaped part having an exterior surface comprising said electrically conductive surface.

10. An electrode device as claimed in claim 8 wherein at least one of said moveable parts has a curved section.

11. An electrode device as claimed in claim 8 wherein said electrode cable has a longitudinal axis extending along a length thereof, wherein each of said moveable parts has a rear end extending immediately behind said electrode head, and wherein said control means comprises a conical element abutting said rear ends of said moveable parts, and wherein said means for changing the position of said control means comprises means for advancing said conical element along said longitudinal axis towards said electrode head for mechanically interacting with said rear ends of said moveable parts to change the distance between the conductive surfaces.

* * * * *